(12) United States Patent
Itoh et al.

(10) Patent No.: US 6,713,492 B1
(45) Date of Patent: Mar. 30, 2004

(54) N-ACYLOXYLATED CYCLOALKYL COMPOUNDS, COMPOSITION CONTAINING THE SAME AND METHODS OF USE THEREFOR

(75) Inventors: Osamu Itoh, Yamagata (JP); Heitaro Obara, Sendai (JP); Hidekatsu Yokoyama, Koriyama (JP); Masaaki Aoyama, Yamagata (JP)

(73) Assignees: Daiichi Radioisotope Laboratories, Ltd., Tokyo (JP); Yamagata Public Corporation for the Development of Industry, Yamagata (JP)

( * ) Notice: Subject to any disclaimer, the term of this patent is extended or adjusted under 35 U.S.C. 154(b) by 0 days.

(21) Appl. No.: 09/831,898

(22) PCT Filed: Nov. 22, 1999

(86) PCT No.: PCT/JP99/06523

§ 371 (c)(1),
(2), (4) Date: May 24, 2001

(87) PCT Pub. No.: WO00/30638

PCT Pub. Date: Jun. 2, 2000

(30) Foreign Application Priority Data

Nov. 25, 1998 (JP) ............................................. 10-334340

(51) Int. Cl.$^7$ ...................... A01N 43/90; A01N 43/40; C07D 211/22; C07D 211/06; C07D 211/78
(52) U.S. Cl. ...................... 514/317; 514/327; 514/328; 514/329; 514/330; 514/345; 514/346; 514/348; 514/350; 514/354; 514/423; 546/219; 546/221; 546/222; 546/223; 546/224; 546/225; 546/226; 546/242; 546/244; 546/245; 546/290; 546/292; 546/297; 546/298; 546/299; 548/531; 548/536; 548/565
(58) Field of Search .................. 546/219, 221, 546/222, 223, 224, 225, 226, 242, 244, 245, 290, 293, 297, 298, 299; 548/531, 536, 565; 514/317, 327, 328, 329, 330, 345, 346, 348, 350, 354, 423

(56) References Cited

U.S. PATENT DOCUMENTS

| | | | |
|---|---|---|---|
| 4,902,699 A | 2/1990 | Toja et al. ................ | 514/357 |
| 5,004,770 A | 4/1991 | Cortolano et al. | |
| 5,053,416 A | 10/1991 | Toja et al. ................ | 514/340 |
| 5,124,378 A | 6/1992 | Behrens et al. | |

FOREIGN PATENT DOCUMENTS

| | | | |
|---|---|---|---|
| EP | 0 309 400 | 3/1989 | |
| EP | 0 365 481 | 4/1990 | |
| WO | WO 96/15110 | 5/1996 | |
| WO | WO 98/01426 | 1/1998 | ................ 514/340 |
| WO | WO 99/05108 | 2/1999 | |

OTHER PUBLICATIONS

S. Dikalov, et al., Biochem. Biophys. Res. Commun., vol. 230, pp. 54–57, "Quantification of Peroxynitrite, Superoxide, and Peroxyl Radical by a New Spin Trap Hydroxyamine, 1–Hydroxy–2,2,6,6,– Tetramethyl–4–Oxo–Piperidine", 1997.

L. L. Martin, et al., J. Med. Chem., vol. 22, No. 11, pp. 1347–1354, "Synthesis of Spiro [Isobenzofuran–1 (3H), 4'–Piperidines] as Potential Central Nervous System Agents. 5. Conformationally Mobile Analogs Derived by Furan Ring Opening", 1979.

K. Kobayashi, et al., Bull. Chem. Soc. Jpn., vol. 68, No. 5, pp. 1401–1407, "Reactions of Sulfoxides with Magnesium Amides. Transformation of Sulfoxides Into Sulfides, Dithioacetals, and Vinyl Sulfides", 1995.

D. Crich, et al., J. Am. Chem. Soc., vol. 116, No. 20, pp. 8937–8951, "Photoinduced Free Radical Chemistry of the Acyl Tellurides: Generation, Inter– and Intramolecular Trapping, and ESR Spectroscopic Identification of Acyl Radicals", 1994.

F. Cinget, et al., J. Carbohydr. Chem., vol. 11, No. 7, pp. 921–931, "Novel Synthesis of 2, 2, 6, 6–Tetramethylpiperidin–1–Oxyl–4–YL–. Beta .–D–Glucopyrano Side and Its Peracetyl Derivative", 1992.

C. Chen, et al., J. Am. Chem. Soc., vol. 114, No. 21, pp. 8313–8314, "The Chemistry of Acyl Tellurides: Generation and Trapping of Acyl Radicals, Including Aryltellurium Group Transfer", 1992.

Green, S. A., et al., "Intramolecular Quenching of Excited Singlet States by Stable Nitroxyl Radicals", Journal of the American Chemical Society, American Chemical Society, Washington, DC, US, vol. 112, No. 20, 1990, pp. 7337–7346.

Yordanov, A.T., "Acyl–Protected Hydroxylamines as Spin Label Generators for EPR Brain Imaging", Journal F. Medicinal Chemistry, 2002 pp. 2283–2288.

*Primary Examiner*—Alan L. Rotman
*Assistant Examiner*—Raymond Covington
(74) *Attorney, Agent, or Firm*—Oblon, Spivak, McClelland, Maier & Neustadt, P.C.

(57) ABSTRACT

Drugs or reagents containing as the active ingredient N-acyloxylated cycloalkyl compounds represented by general formula (I):

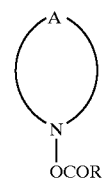

(I)

wherein A is optionally substituted $C_4$ or $C_5$ cycloalkyl which may have one double bond in the ring; and R is $C_1$–$C_3$ alkyl or phenyl). The above compounds are hydroxyamine derivatives functioning as spin trapping agents and can rapidly react with free radicals or active oxygen in an objective organ in spite of their being excellent in stability during the preparation or administration thereof.

23 Claims, 3 Drawing Sheets

N-ACYLOXYLATED CYCLOALKYL COMPOUNDS, COMPOSITION CONTAINING THE SAME AND METHODS OF USE THEREFOR

TECHNICAL FIELD

The present invention relates to a drug comprising a modified N-acyloxylated cycloalkyl compound as an effective ingredient and, more particularly, to a drug comprising an N-acyloxylated cycloalkyl compound which can scavenge in vivo active oxygen or free radicals and is useful as an agent for preventing or curing various diseases induced by in vivo active oxygen or free radicals and as a reagent for non-invasively acquiring biological images by a magnetic resonance method, typified by the ESR (Electron Spin Resonance) method, or for detecting in vivo active oxygen or free radicals in collected organisms.

BACKGROUND ART

Active oxygen is defined as one type of oxygen species with a short life which is very reactive and takes part in various types of in vivo oxidation reactions. The scope of active oxygen varies depending on the definition. In a narrow sense, active oxygen means a hydroxyl radical (.OH), superoxide ($O_2^-$), singlet oxygen ($^1O_2$), and hydrogen peroxide ($H_2O_2$). In a broad sense, active oxygen includes a peroxy radical (LOO.) and alkoxy radical (LO.) which are derived from the reaction of the above active species and biological components such as unsaturated fatty acid L, and a hypochlorite ion ($ClO^-$) formed from $H_2O_2$ and $Cl^-$ by the reaction with myeloperoxidase and the like.

Radicals are defined as atoms or molecules which possess one or more unpaired electrons. A hydroxyl radical, superoxide, peroxy radical, and alkoxy radical are all radicals. Singlet oxygen and hydrogen peroxide are not radicals, but are formed from a radical reaction or cause other radical reactions.

In recent years, active oxygen and free radicals showing various in vivo bioactivity have attracted attention and have been studied in the field of biology, medicine, and pharmacology. The active oxygen or free radicals are generated in vivo due to ultraviolet rays, radiation, atmospheric pollution, oxygen, metal ions, ischemia-reperfusion, and the like. Active oxygen and free radicals thus generated cause various in vivo reactions such as peroxidization of lipids, denaturation of proteins, and decomposition of nucleic acids. Ischemic diseases, digestive diseases, cancer, cranial nervous diseases accompanied by nerve degeneration, inflammation, cataracts, and drug-induced organopathy are known as diseases accompanied by such phenomena. Non-invasive detection of such active oxygen and free radicals which relate to so many diseases may help in the investigation of the causes of a number of such diseases and provide useful medical information.

The following two methods are known as conventional methods for detecting free radicals. One of these is an indirect method consisting of adding a reagent to a reaction system and detecting the resulting changes in absorbance or emission of light by the reaction system. The other method is an electron spin resonance (ESR) method consisting of directly detecting unpaired electron of free radicals. Since the ESR method can measure both liquid and solid samples and even opaque or non-uniform samples, this method is very advantageous for detecting active oxygen in collected biological samples or in vivo.

The problem in detecting in vivo active oxygen or free radicals is that ESR cannot directly measure active oxygen or free radicals in a living body due to their short life. To solve this problem, a method of indirectly observing in vivo active oxygen or free radicals by administering a reagent to a living body and measuring the chemical changes in the reagent caused by active oxygen or free radicals using ESR has been employed. For this purpose, a spin trapping method has been developed with an objective of measuring active oxygen having unpaired electrons such as hydroxyl radicals. This method makes use of the capability of a trapping agent to rapidly react with free radicals having only a short life and produce a spin adduct which is stable, has a long life, and can be detected by ESR, as shown in the following formula. In a narrow sense, the spin trapping agent has been defined as a compound having a double bond in the scavenging site, such as 5,5-dimethyl-1-pyrroline-1-oxide (DMPO) shown below.

Spin trapping agent (No ESR signals)    In vivo radicals or free radicals (short life)    Spin adduct (with ESR signals)

Specifically, measurement of short-life active oxygen becomes possible by adding a compound which can rapidly react with radicals and produces a spin adduct sufficiently stable for measuring ESR to the measuring system as a spin trapping agent, and measuring the stable spin adduct.

Therefore, the requirements to be satisfied by the compound used as a spin trapping agent include: (1) capability of rapidly reacting with active oxygen and free radicals, (2) being converted into sufficiently stable radicals, (3) being chemically stable when handled, and (4) being free from toxicity.

An attempt to directly detect or image in vivo active oxygen or free radicals by using the above spin trapping agent has been undertaken. However, large volume biological samples cannot be measured using conventional ESR devices which utilize microwaves of an X-band (about 9.5 GHz) due to high dielectric loss in water.

In recent years, ESR-CT utilizing low-frequency microwaves (300–2000 MHz) has been developed, making it possible to directly detect or image free radicals in a sample containing a large amount of water, particularly, free radicals in a living body.

The principle of a nuclear magnetic resonance (NMR) method was discovered in 1945. In 1973, Lauterbur first applied the NMR method to magnetic resonance imaging (MRI) which is an imaging device used in medicine. Since then, the NMR method has progressed remarkably and becomes one of the most universal diagnostic methods at present.

MRI first appeared as a diagnostic method using no contrast media. At present, contrast media are used to increase the detectability of a lesion site which is difficult to shade. Therefore, contrast media exhibiting superior detectability are demanded.

In recent years, the utility of nitroxide compounds as contrast media for MRI or ESR and the antioxidation effect thereof has attracted attention. For example, paramagnetic inorganic compounds such as gadolinium are administered as contrast media to contrast the lesion site in the MRI diagnosis used in medicine. However, because of toxicity of such inorganic compounds, nitroxide compounds have been considered as MRI contrast media which can be used instead of gadolinium. As ESR imaging has been developed and the utility thereof has attracted attention, the utility value of nitroxide compounds as imaging agents has increased. The possibility of utilization of nitroxide compounds as an active oxygen scavenging agent has also been suggested (see J. Biol. Chem. 263: 17921; 1998).

If information about active oxygen or free radicals in biological tissue can be acquired as biological images by the noninvasive magnetic resonance measuring method, this information can be used for studying pathology in which active oxygen and free radicals take part, such as ischemic diseases, digestive diseases, cancer, cranial nervous diseases accompanied by nerve degeneration, inflammation, cataracts, and drug-induced organopathy (hereinafter referred to "diseases related to active oxygen and the like") and diagnosing these diseases.

In this situation, a report has been published describing the characteristics of some type of hydroxylamine derivative which can easily react with free radicals and active oxygen by oxidative stimulation (active oxygen, etc.) and be converted into a nitroxide compound having ESR signals (Biochem Biophys Res Commun 230, 54–57, 1997). The compound is not a spin trapping agent in the stringent sense because this is not a generally defined nitron or nitroso compound. However, inasmuch as the capability of scavenging spins as shown by the following formula, the compound has the same function as the spin trapping agent in a narrow sense.

In the above formula, A' represents an alkylene group which may be substituted.

Although it has been known that super oxide in solutions or cells can be detected by measuring the ESR signals of the nitroxide compound formed by the above reaction, the hydroxylamine derivatives presented a serious problem in applying the above reaction to the detection of active oxygen and free radicals. Specifically, although nitroxide compounds derived from hydroxylamine derivatives are such stable compounds that these compounds can be stored for several weeks in an aqueous solution and crystals thereof can be stored for several years in a desiccator (see, for example, Arch. Biochem. Biophys. 215: 367–378; 1982), the hydroxylamine derivatives themselves are unstable and must be prepared each time they are used.

For this reason, although a certain hydroxylamine derivative has been used for the detection of free radicals or active oxygen in solutions or cells, there have been no examples of acquiring images of free radicals and active oxygen generated in the organs by in vivo administration of a hydroxylamine derivative. The reason why this image acquisition has not been successful is considered to be because the in vivo reaction of the hydroxylamine derivative and free radicals is so fast that the hydroxylamine derivative is metabolized in blood before reaching the organs.

Therefore, development of a technology using a hydroxyamine derivative, which functions as a spin trapping agent and can rapidly react with free radicals or active oxygen in an objective organ and yet exhibit excellent stability during preparation or administration, has been desired.

DISCLOSURE OF THE INVENTION

In order to solve the above problems, the inventors of the present invention have conducted extensive studies to discover a compound which is itself stable, rapidly reacts with active oxygen and free radicals in living bodies producing stable products, and possesses guaranteed safety in living bodies. As a result, the inventors have found that an N-acyloxy cycloalkyl compound obtained by acylating the hydroxyl group of a certain hydroxylamine derivative satisfies the above requirements, can scavenge free radicals and active oxygen, and can be effectively used for the detection or deletion of such free radicals and active oxygen.

Acquiring images of free radicals and active oxygen by spin trapping has conventionally been considered to be difficult. However, since the above N-acyloxylated cycloalkyl compound is a compound produced by stabilizing a hydroxylamine derivative having the same function as a spin trapping agent, this compound is stable after preparation and can be transferred to the target organs without being metabolized after administration. The compound is then hydrolyzed into the hydroxylamine derivative, which reacts with active oxygen or free radicals in the organ to produce a nitroxide emitting ESR signals. The inventors have found that images of active oxygen or free radicals can be acquired by detecting the ESR signals.

The inventors have further found that the N-acyloxylated cycloalkyl compound can scavenge active oxygen and free radicals, and can be used as a preventive or therapeutic agent for diseases such as ischemic diseases, digestive diseases, cancer, cranial nervous diseases accompanied by nerve degeneration, inflammation, cataracts, or drug-induced organopathy, as a drug such as an image diagnosis agent or a detection reagent, and the like.

Accordingly an object of the present invention is to provide a drug or reagent containing an N-acyloxylated cycloalkyl compound shown by the following formula (1) as an effective ingredient, (I)

wherein A represents a $C_4$ or $C_5$ alkylene group which may have one double bond in the ring and may be substituted with an alkyl group, amino group, amide group, carbamoyl group, carboxyl group, keto group, hydroxyl group, sulfonic acid group, phenyl group, acetoxyl group, or acetoamino group, and R is a $C_1$–$C_3$ alkyl group or phenyl group.

Another object of the present invention is to provide a method of scavenging in vivo active oxygen or free radicals comprising administering the above N-acyloxylated cycloalkyl compound (I).

Still another object of the present invention is to provide a novel N-acyloxylated cycloalkyl compound represented by the following formula (II'), wherein m is 0 or 1; when m is 0, X' and Y' individually represent a hydrogen atom, alkyl group, amino group, amide group, carbamoyl group, carboxyl group, keto group, hydroxyl group, sulfonic acid group, phenyl group, acetoxyl group, or acetoamino group, and when m is 1, X' and Y' individually represent a hydrogen atom, alkyl group, amino group, amide group, carbamoyl group, carboxyl group, keto group, hydroxyl group, sulfonic acid group, phenyl group, or acetoamino group; R is a $C_1$–$C_3$ alkyl group or a phenyl group; $R^1$, $R^2$, $R^3$, and $R^4$ individually represent a $C_1$–$C_4$ alkyl group; and

===== represents a single bond or double bond.

BEST MODE FOR CARRYING OUT THE INVENTION

The N-acyloxylated cycloalkyl compound (I) of the present invention can be prepared by reducing the nitroxide compound shown by the formula (III) into a hydroxylamine compound shown by the formula (IV), and esterifying the hydroxylamine compound by the carboxylic acid shown by the formula (V) or its reactive derivative according to the following reaction:

wherein A represents a $C_4$ or $C_5$ alkylene group which may have one double bond in the ring and may be substituted with an alkyl group, amino group, amide group, carbamoyl group, carboxyl group, keto group, hydroxyl group, sulfonic acid group, phenyl group, acetoxyl group, or acetoamino group, and R is a $C_1$–$C_3$ alkyl group or phenyl group.

In the above reaction, the nitroxide compound (III) used as the starting raw material is a known compound or a compound prepared by a known method (for example, the method of A. M. Feldman et al. (U.S. Pat. No. 3,334,103) or the method of W. Bueschken et al. (DP 4219459). The following compounds can be given as specific examples of the nitroxide compound (III).

Although the reduction of the nitroxide compound (III) can be carried out according to a conventional method, a method of dissolving the nitroxide compound (III) in methanol and reducing the compound by. the addition of hydrazine monohydrate is preferably employed.

Esterification of the hydroxylamine compound (VI) obtained by the reduction of the nitroxide compound (III) can also be carried out according to a conventional method. One example of such a method comprises the reaction of the hydroxylamine compound (VI) with the carboxylic acid (V) in the presence of a dehydration condensation catalyst. A method of using a derivative of the carboxylic acid (V) such as an active ester, acid anhydride, acid halide, and the like is also effective.

As a preferable example of the above compound (I), N-acyloxylated cycloalkyl compound represented by the following formula (II) can be given.

wherein X and Y individually represent a hydrogen atom, alkyl group, amino group, amide group, carbamoyl group, carboxyl group, keto group, hydroxyl group, sulfonic acid group, phenyl group, acetoxyl group, or acetoamino group, and R is a $C_1$–$C_3$ alkyl group or a phenyl group, $R^1$, $R^2$, $R^3$, and $R^4$ individually represent a $C_1$–$C_4$ alkyl group, and

----- represents a single bond or double bond, and m indicates 0 or 1.

Among the N-acyloxylated cycloalkyl compounds represented by the following formula (II), the compound shown by the following formula (II') is a novel compound, not disclosed in any published document:

(II')

wherein m is 0 or 1; when m is 0, X' and Y' individually represent a hydrogen atom, alkyl group, amino group, amide group, carbamoyl group, carboxyl group, keto group, hydroxyl group, sulfonic acid group, phenyl group, acetoxyl group, or acetoamino group, and when m is 1, X' and Y' individually represent a hydrogen atom, alkyl group, amino group, amide group, carbamoyl group, carboxyl group, keto group, hydroxyl group, sulfonic acid group, phenyl group, or acetoamino group; R is a $C_1$–$C_3$ alkyl group or a phenyl group; $R^{1'}$, $R^{2'}$, $R^3$, and $R^4$ individually represent a $C_1$–$C_4$ alkyl group; and

----- represents a single bond or double bond, provided that when both X' and Y' are a hydrogen atom, R is neither a phenyl group nor a methyl group, and when X' is a hydrogen atom and Y' is a hydroxyl group, R is not a methyl group.

Drugs or reagents for administration are prepared using the N-acyloxylated cycloalkyl compound (I) of the present invention thus obtained by dissolving the compound in a pharmaceutically or chemically acceptable solvent such as a physiological saline solution or isotonic phosphate buffer solution and adding optional components such as propylene glycol or benzyl alcohol as required.

Drugs or reagents using the N-acyloxylated cycloalkyl compound (I) of the present invention are preferably prepared as injections, drops, liniments, eye drops, and the like.

Drugs using the N-acyloxylated cycloalkyl compound (I) of the present invention include diagnostic drugs. Such diagnostic drugs are used as a drug for diagnosing diseases relating to the active oxygen which detect the presence of the active oxygen or free radicals by intravascular administration. For example, such diagnostic drugs are used for contrastradiography for MRI of brain or heart diseases or contrastradiography for ESR.

Although the amount of the N-acyloxylated cycloalkyl compound (I) to be used in the above drugs differs depending on the object or objective organs or diseases, such drugs are generally administered so that the amount of the N-acyloxylated cycloalkyl compound (I) is 0.1–500 mg/kg.

As examples of other usage for drugs, preventive preparations or therapeutic agents for diseases caused by the active oxygen or free radicals in vivo can be given. Such preventive or therapeutic agents, which react with active oxygen or free radicals and eliminate them, are effective for prophylaxis and treatment of the diseases related to active oxygen and the like.

The active oxygen or free radicals generated from the tissue or organs at a normal or diseased state can be detected from outside the body and imaged by administering the above drugs to normal animals and diseased model experimental animals. The drugs can be used as detection reagents for determining what active oxygen and free radicals relate to what kind of diseases from the results of imaging, thereby providing useful medical information.

Furthermore, the drugs can be used as detection reagents for measuring the presence or absence, or the amount of active oxygen or free radicals in biological tissues by homogenizing collected samples, adding an appropriate buffer solution and the drugs to the homogenized solution, allowing the mixture to react for a certain period of time, and measuring the ESR.

The present invention will be described in more detail by way of examples, which should not be construed as limiting the present invention.

EXAMPLE 1

Synthesis of 1-Acetoxy-3-carbamoyl-2,2,5,5-tetramethylpyrrolidine (1) Synthesis of 1-Hydroxy-3-carbamoyl-2,2,5,5-tetramethylpyrrolidine 1.0 g (5.4 mmol) of 3-carbamoyl-2,2,5,5-tetramethyl-pyrrolidine-1-yloxy was dissolved in 50 ml of methanol. After the addition of 10 ml of hydrazine monohydrate, the mixture was reacted for 6 hours at room temperature while stirring. The solvent was evaporated under vacuum to obtain 1.0 g (5.4 mmol, yield: 100%) of white crystals.

Melting point: 230–234° C. (decomposed) $^1$H-NMR(in DMSO; δ): 0.88, s, 3H ($CH_3$), 1.02, s, 3H ($CH_3$), 1.07, s, 3H ($CH_3$), 1.14, s, 3H ($CH_3$), 1.52, dd (J=12.4 Hz, J=8.1 Hz), 1H ($CH_2$), 1.96, t (J=11.8 Hz), 1H ($CH_2$), 2.48, dd (J=11.8 Hz, J=8.7 Hz), 1H(CH), 6.81, s, 1H($CONH_2$), 7.12, s, 1H(OH), 7.15, s, 1H($CONH_2$)

(2) Synthesis of 1-Acetoxy-3-carbamoyl-2,2,5,5-tetramethylpyrrolidine 20 ml of dichloromethane and 3 ml of triethylamine were added to 0.50 g (2.7 mmol) of 1-hydroxy-3-carbamoyl-2,2,5,5-tetramethylpyrrolidine. 0.38 ml (4.0 mmol) of acetic anhydride was added dropwise to the mixture with stirring and ice-cooling, the mixture was stirred for 3 hours. The reaction mixture was washed with water, 3% diluted hydrochloric acid, water, 5% sodium hydrogencarbonate aqueous solution, and water, in this order. The organic layer was dried over magnesium sulfate, and the solvent was evaporated under vacuum. The residue was purified by silica gel column chromatography (ethyl acetate) and recrystallized from ethyl acetate to obtain 0.53 g (2.3 mmol) of white crystals (yield: 86%).

Melting point: 150–151° C. $^1$H-NMR (in DMSO; δ): 0.97, s, 3H ($CH_3$), 1.10, s, 3H ($CH_3$), 1.12, s, 3H ($CH_3$), 1.15, s, 3H ($CH_3$), 1.64, dd (J=12.4 Hz, J=7.4 Hz), 1H ($CH_2$), 2.06, s, 3H ($COCH_3$), 2.07, br, 1H (CH2), 2.62, br, 1H (CH), 6.94, s, 1H ($CONH_2$), 7.27, s, 1H ($CONH_2$) Mass spectrum (EI$^+$): m/z 228.3 (M$^+$)

EXAMPLE 2

Synthesis of 1-Propionyloxy-3-carbamoyl-2,2,5,5-tetramethylpyrrolidine 0.56 g (2.3 mmol) of white crystals were prepared in the same manner as in Example 1(2), except for using 0.52 ml of propionilc anhydride instead of 0.38 ml of acetic anhydride (yield: 85%).

Melting point: 116–117° C. $^1$H-NMR(in DMSO; δ): 0.97, s, 3H(CH$_3$), 1.06, t (J=7.4 Hz), 3H(CH$_3$), 1.09, s, 3H (CH$_3$), 1.11, s, 3H (CH$_3$) 1.14, s, 3H (CH$_3$), 1.64, dd (J=12.4 Hz, J=7.4 Hz), 1H (CH$_2$) , 2.12, br, 1H(CH$_2$), 2.36, q (J=7.4 Hz, 2H (CH$_2$), 2.62, br, 1H (CH), 6.94, s, 1H (CONH$_2$), 7.27, s, 1H (CONH$_2$) Mass spectrum (EI$^+$): m/z 242.3 (M$^+$)

EXAMPLE 3

Synthesis of 1-Butylyloxy-3-carbamoyl-2,2,5,5-tetramethylpyrrolidine 0.61 g (2.4 mmol) of white crystals were prepared in the same manner as in Example 1(2), except for using 0.66 ml of butyric anhydride instead of 0.38 ml of acetic anhydride (yield: 88%).

Melting point: 103–104° C. $^1$H-NMR (in DMSO; δ): 0.91, t (J=7.4 Hz), 3H (CH$_3$), 0.97, s, 3H (CH$_3$), 1.09, s, 3H (CH$_3$), 1.11, s, 3H (CH$_3$), 1.14, s, 3H (CH$_3$), 1.58, sex (J=7.4 Hz), 2H (CH$_2$), 1.64, dd (J=12.4 Hz, J=7.4 Hz), 1H (CH$_2$), 2.12, br, 1H (CH$_2$), 2.32, t (J=7.4 Hz), 2H (CH$_2$), 2.62, br, 1H (CH), 6.94, s, 1H (CONH$_2$), 7.27, s, 1H (CONH$_2$) Mass spectrum (EI$^+$): m/z 256.3 (M$^+$)

EXAMPLE 4

Synthesis of 1-Benzoyloxy-3-carbamoyl-2,2,5,5-tetramethylpyrrolidine 0.72 g (2.5 mmol) of white crystals were prepared in the same manner as in Example 1(2), except for using 0.76 ml of benzoic anhydride instead of 0.38 ml of acetic anhydride (yield: 92%).

Melting point: 199–201° C. $^1$H-NMR (in DMSO; δ) 1.10, s, 3H (CH$_3$), 1.20, br, s, 12H (CH$_3$×3), 1.72, dd (J=12.4 Hz, J=7.4 Hz),1H (CH$_2$), 2.22, br, 1H (CH$_2$), 2.72, br, 1H(CH), 6.99, s, 1H (CONH$_2$), 7.32, s, 1H (CONH$_2$), 7.56, t (J=8.1 Hz), 2H (ARH), 7.68, t (J=7.4 Hz), 1H (ARH), 7.97, dd (J=8.1 Hz, J=1.2 Hz), 2H(ARH) Mass spectrum (EI$^+$): m/z 290.4 (M$^+$)

EXAMPLE 5

Synthesis of 1,4-Diacetoxy-2,2,6,6-tetramethylpiperidine (1) Synthesis of 1,4-Dihydroxy-2,2,6,6-tetramethylpiperidine 1.0 g (5.8 mmol) of 4-hydroxy-2,2,6,6-tetramethylpiperidine-1-yloxy was dissolved in 50 ml of methanol. After the addition of 10 ml of hydrazine monohydrate, the mixture was reacted for 6 hours at room temperature while stirring. The solvent was evaporated under vacuum to obtain 1.0 g (5.8 mmol, yield: 100%) of white crystals.

Melting point: 167–168° C. (decomposed) $^1$H-NMR (in DMSO; δ): 1.02, s, 6H (CH$_3$×2), 1.04, s, 6H (CH$_3$×2), 1.24, t (J=11.8 Hz), 2H (CH$_2$), 1.70, dd (J=11.8 Hz, J=3.1 Hz), 2H (CH$_2$), 3.74, m, 1H (CH), 4.38, d (J=5.0 Hz), 1H (OH), 7.01, s, 1H (N—OH)

(2) Synthesis of 1,4-Diacetoxy-2,2,6,6-tetramethylpiperidine 9

20 ml of dichloromethane and 3 ml of triethylamine were added to 0.50 g (2.9 mmol) of 1,4-dihydroxy-2,2,6,6-tetramethylpiperidine. 0.80 ml (2.9 mmol) of acetic anhydride was added dropwise to the mixture with stirring and ice-cooling, the mixture was stirred for 3 hours. The reaction mixture was washed with water, 3% diluted hydrochloric acid, water, 5% sodium hydrogencarbonate aqueous solution, and water, in this order. The organic layer was dried over. magnesium sulfate, and the solvent was evaporated under vacuum. The residue was purified by silica gel column chromatography (ethyl acetate) to obtain 0.57 g (2.2 mmol) of white crystals (yield: 76%).

Melting point: 72–73° C. $^1$H-NMR (in DMSO; δ): 1.00, s, 6H (CH$_3$×2), 1.17, s, 6H (CH$_3$×2), 1.54, t (J=11.8 Hz), 2H (CH$_2$), 1.91, dd (J=11.8 Hz, J=3.1 Hz), 2H (CH$_2$), 1.99, s, 3H (C—OCOCH$_2$), 2.06, s, 3H(N—OCOCH$_3$), 4.98, m, 1H (CH) Mass spectrum (EI$^+$): m/z 257.3 (M$^+$)

EXAMPLE 6

Synthesis of 1-Acetoxy-4-acetamide-2,2,6,6-tetramethylpiperidine (1) Synthesis of 1-Hydroxy-4-amino-2,2,6,6-tetramethylpiperidine 1.0 g (5.8 mmol) of 4-amino-2,2,6,6-tetramethyl-piperidine-1-yloxy was dissolved in 50 ml of methanol. After the addition of 10 ml of hydrazine monohydrate, the mixture was reacted for 6 hours at room temperature while stirring. The solvent was evaporated under vacuum to obtain 1.0 g (5.8 mmol, yield: 100%) of white crystals.

Melting point: 115–117° C. (decomposed) $^1$H-NMR (in DMSO; δ): 1.00, s, 6H (CH$_3$×2), 1.01, s, 6H (CH$_3$×2), 1.10, t (J=11.8 Hz), 2H (CH$_2$), 1.59, d (J=9.9 Hz), 2H (CH$_2$), 2.84, m, 1H (CH), 7.05, s, 1H (N—OH)

(2) Synthesis of 1-Acetoxy-4-acetamide-2,2,6,6-tetramethylpiperidine 20 ml of dichloromethane and 3 ml of triethylamine were added to 0.50 g (2.9 mmol) of 1-hydroxy-4-amino-2,2,6,6-tetramethylpiperidine. 0.80 ml (8.4 mmol) of acetic anhydride was added dropwise to the mixture with stirring and ice-cooling, the mixture was stirred for 3 hours. The reaction mixture was washed with water, 3% diluted hydrochloric acid, water, 5% sodium hydrogencarbonate aqueous solution, and water, in this order. The organic layer was dried over magnesium sulfate, and the solvent was evaporated under vacuum. The residue was purified by silica gel column chromatography (ethyl acetate) and recrystallized from ethyl acetate-hexane to obtain 0.54 g (2.1 mmol) of white crystals (yield: 72%).

Melting point: 115–117° C. $^1$H-NMR (in DMSO; δ) 0.96, s, 6H (CH$_3$×2), 1.14, s, 6H (CH$_3$×2), 1.40, t(J=12.4 Hz), 2H (CH$_2$), 1.69, d (J=12.4 Hz), 2H (CH$_2$), 1.78, s, 3H (C—OCOCH$_2$), 2.05, s, 3H (N—OCOCH$_2$), 3.97, m, 1H (CH), 7.74, d (J=8.1 Hz), 1H (NHCO) Mass spectrum (EI$^+$): m/z 256.4 (M$^+$)

EXAMPLE 7

Test for Measuring Enzyme Activity

Figure 1:
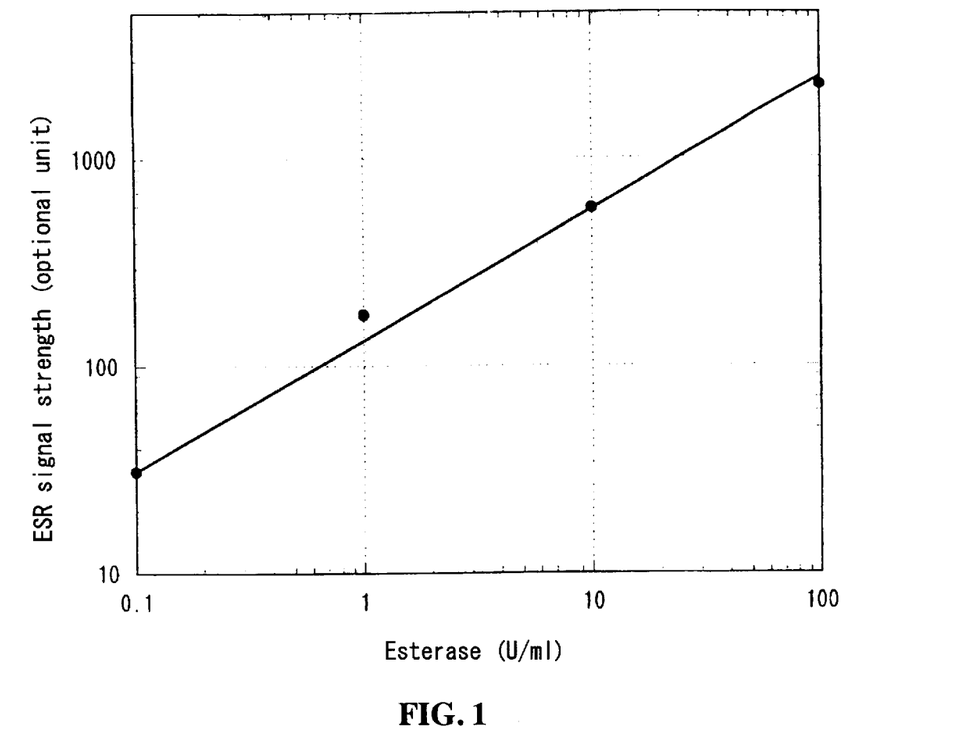
FIG. 1 shows a calibration line used for the determination of the esterase concentration in a solution by the ESR signal strength using 1-acetoxy-3-carbamoyl-2,2,5,5-tetramethylpyrrolidine.

Capability of enzyme (esterase) activity determination by ESR using 1-acetoxy-3-carbamoyl-2,2,5,5-tetramethylpyrrolidine was examined. Esterase (3360 U/ml, manufactured by Sigma Co., Esterase, Porcine Liver) was diluted with a phosphate buffered saline solution (pH7.4, 67 mM) to concentrations of 0.2, 2, 20, and 200 U/ml. 100 μl of each diluent was added to 100 μl of a 1 mM sample solution, and allowed to stand for one minute. Specifically, the sample was converted into a hydroxylamine derivative using the esterase. Next, 10 μl of 10 mM sodium periodide phosphate buffered saline solution was added. Specifically, the hydroxylamine derivative produced was converted into a nitroxide derivative which can be measured by ESR. Finally, this solution is suctioned into a flat cell (manufactured by Labotech Co.) to measure ESR spectrum using "JES-REIX" manufactured by JEOL Ltd after one minute. The relation between the signal strength of the ESR spectrum obtained and the esterase concentration is shown in FIG. 1.

The result confirmed that the sample material is hydrolyzed by esterase in a short time and the reaction is quantitative. In addition, it was confirmed that the esterase activity can be measured by using this reaction.

EXAMPLE 8

Measurement of ESR-CT Image of Rat Brain 6 ml of 150 mM physiological saline solution of 1-acetoxy-3-carbamoyl-2,2,5,5-tetramethylpyrrolidine was intraperitoneally administered to Wister male rats (200 g, age: nine weeks) anesthesized with pentobarbital. The head of the rat was secured so that the part of the head 9 mm ahead of the external auditory meatus came to the center of the resonator. ESR-CT was measured 20 minutes after administration. The measuring conditions of ESR-CT were as follows.
(Measurement Conditions of ESR-CT)
    Instrument: 700 MHz band electron spin resonance apparatus
    Microwave frequency: 720 MHz
    Microwave power: 52 mW
    Central magnetic field: 25 mT
    Magnetic field sweep width: 15 mT
    Magnetic field modulation width: 0.2 mT
    Magnetic field modulation frequency: 100 kHz
    Magnetic field gradient: 1 mT/cm
    Magnetic field gradient rotational angle: 20°

Figure 2:
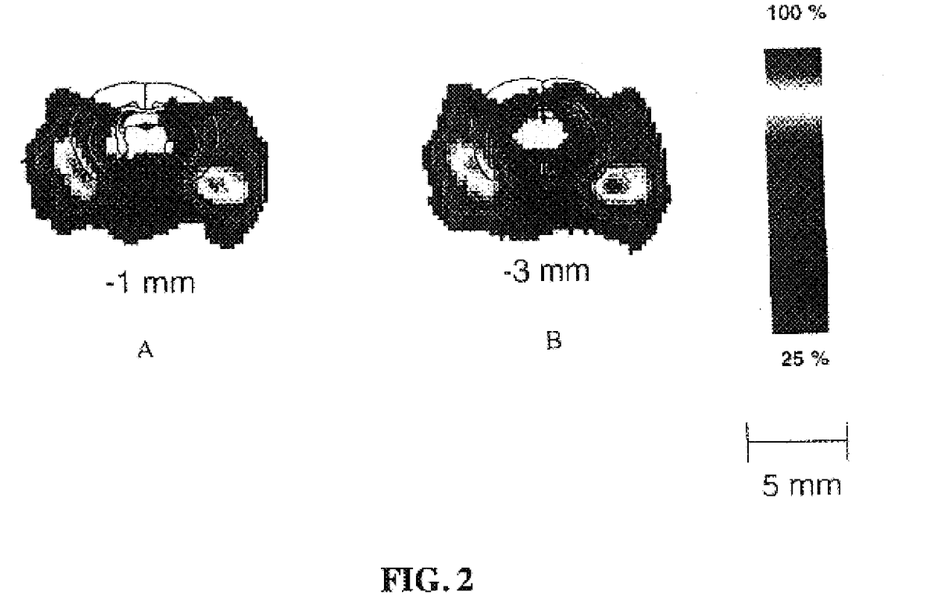
FIG. 2 shows an ESR-CT image of the brain of a rat to which 1-acetoxy-3-carbamoyl-2,2,5,5-tetramethylpyrrolidine has been administered and the positional relationship in the brain.
Figure 3:
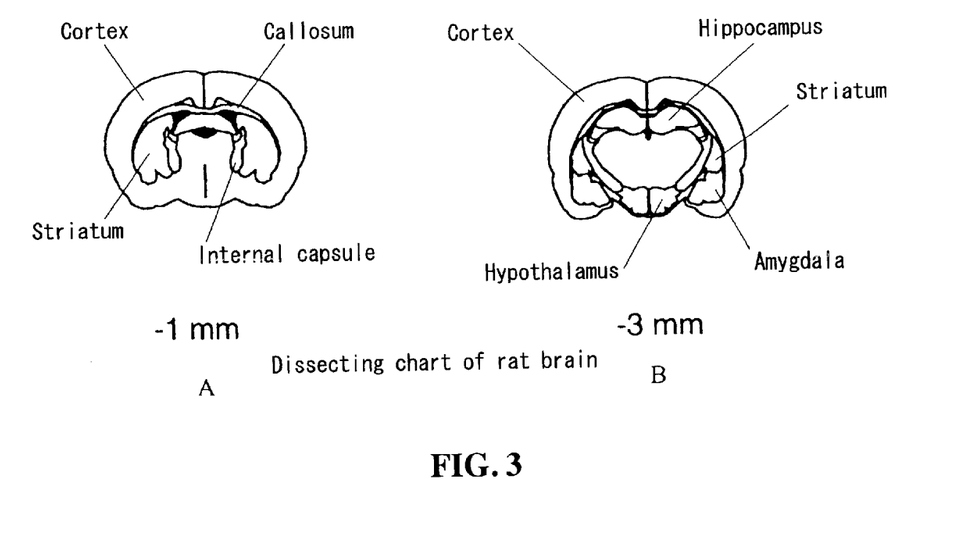
FIG. 3 is a drawing describing the part of the brain indicated by the anatomical chart shown in FIG. 2.

The measured black-and-white picture image is shown in FIG. 2, and a color picture image is attached as a reference figure. In FIG. 2, A is a rat brain ESR-CT image 1 mm posterior to the bregma, and B is a rat brain ESR-CT image 3 mm posterior to the bregma. FIG. 3 is a drawing describing the part of the brain indicated by the anatomical chart in FIG. 2.

Nitroxide radical signals were observed in the hippocampus, cortex, striatum, amygdala, and hypothalamus of the brain, and the rat brain ESR-CT images were acquired based on the signals. The experiment confirmed that a modified hydroxylamine derivative is hydrolyzed after being transferred to the brain, and oxidized by intracerebral active oxygen and free radicals into a nitroxide derivative which emits ESR signals, whereby images of free radicals or active oxygen can be acquired.

INDUSTRIAL APPLICABILITY

The N-acyloxylated cycloalkyl compound (modified hydroxylamine compound) of the present invention which are active ingredients of the diagnostic agent have enough half-life in blood and interact with active oxygen or free radicals in vivo. Therefore, the nitroxide compounds are useful for acquiring biological images of the distribution of free radicals by a magnetic resonance method. Accordingly, the diagnostic agent can be used for diagnosing diseases related to active oxygen and the like such as ischemic diseases, digestive diseases, cancer, cranial nervous diseases accompanied by nerve degeneration, inflammation, cataracts, or drug-induced organopathy in which active oxygen or free radicals take part.

Specifically, the above diseases related to active oxygen and the like can be diagnosed by administering the diagnostic agent containing the N-acyloxylated cycloalkyl compound of the present invention to the living body, and detecting the signal change of the nitroxide compounds in vivo by ESR, NMR, and the like.

Therefore, the diagnostic agent of the present invention is used for MRI. If ESR devices capable of measuring large content biological samples such as a human body are developed, the diagnostic agent non-invasively diagnoses the diseases or symptoms in which active oxygen takes part by acquiring the images of free radical distribution in the human body by the ESR method.

Since the N-acyloxylated cycloalkyl compound of the present invention can react with in vivo active oxygen or free radicals and eliminate them, the compound can be used as a preventive or therapeutic agent for the diseases related to active oxygen and the like.

In addition, the active oxygen or free radicals generated from the tissue or organs in a normal or diseased state can be detected from the outside of the body and imaged by administering the N-acyloxylated cycloalkyl compound to normal experimental animals and diseased model experimental animals. From the results, the compound can be used as detection reagents for determining what kind of diseases active oxygen and free radicals relate, whereby useful medical information is obtained.

Furthermore, the presence or absence or the amount of active oxygen or free radicals in biological tissues can be measured by homogenizing collected samples, adding an appropriate buffer solution and the N-acyloxylated cycloalkyl compound, and measuring the signal strength by ESR after reacting the mixture for a certain period of time.

What is claimed is:

1. A composition suitable for scavenging or detecting active oxygen or free radicals comprising an N-acyloxylated cycloalkyl compound of the following formula (I) and a carrier, wherein A represents a $C_4$ or $C_5$ alkylene group, wherein A may contain one ring double bond, and wherein A may be substituted with a group selected from the group consisting of an alkyl group, amino group, amide group, carbamoyl group, carboxyl group, keto group, hydroxyl group, sulfonic acid group, phenyl group, acetoxyl group, and acetoamino group, and R is a $C_1$–$C_3$ alkyl group or phenyl group.

2. The composition according to claim 1, wherein A represents a $C_4$ alkylene group.

3. The composition according to claim 1, wherein A represents a $C_5$ alkylene group.

4. The composition according to claim 1, wherein the N-acyloxylated cycloalkyl compound is a compound represented by the following formula (II)

wherein X and Y individually represent a hydrogen atom, alkyl group, amino group, amide group, carbamoyl group, carboxyl group, keto group, hydroxyl group, sulfonic acid group, phenyl group, acetoxyl group, or acetoamino group, R is a $C_1$–$C_3$ alkyl group or a phenyl group, $R^1$, $R^2$, $R^3$, and $R^4$ individually represent a $C_1$–$C_4$ alkyl group,

----- represents a single bond or double bond, and m is 0 or 1.

5. The composition according to claim 4, wherein m is 0.
6. The composition according to claim 4, wherein m is 1.
7. The composition according to claim 4, wherein when m is 0, X and Y individually represent a hydrogen atom, alkyl group, amino group, amide group, carbamoyl group, carboxyl group, keto group, hydroxyl group, sulfonic acid group, phenyl group, acetoxyl group, or acetoamino group, and when m is 1, X and Y individually represent a hydrogen atom, alkyl group, amino group, amide group, carbamoyl group, carboxyl group, keto group, hydroxyl group, sulfonic acid group, phenyl group, or acetoamino group, R is a $C_1$–$C_3$ alkyl group or a phenyl group, $R^1$, $R^2$, $R^3$, and $R^4$ individually represent a $C_1$–$C_4$ alkyl group, and

----- represents a single bond or double bond, provided that when both X and Y are a hydrogen atom, R is neither a phenyl group nor a methyl group, and when X is a hydrogen atom and Y is a hydroxyl group, R is not a methyl group.

8. A method of scavenging or detecting active oxygen or free radicals in vivo which comprises administering an N-acyloxylated cycloalkyl compound shown by the following formula (I) in vivo, (I)

wherein A represents a $C_4$ or $C_5$ alkylene group, wherein A may have one ring double bond, and wherein A may be substituted with a substituent selected from the group consisting of an alkyl group, amino group, amide group, carbamoyl group, carboxyl group, keto group, hydroxyl group, sulfonic acid group, phenyl group, acetoxyl group, and acetoamino group, and R is a $C_1$–$C_3$ alkyl group or phenyl group.

9. The method according to claim 8, wherein A represents a $C_4$ alkylene group.
10. The method according to claim 8, wherein A represents a $C_5$ alkylene group.

11. The method according to claim 8, wherein the N-acyloxylated cycloalkyl compound is a compound represented by the following formula (II), (II)

wherein X and Y individually represent a hydrogen atom, alkyl group, amino group, amide group, carbamoyl group, carboxyl group, keto group, hydroxyl group, sulfonic acid group, phenyl group, acetoxyl group, or acetoamino group, R is a $C_1$–$C_3$ alkyl group or a phenyl group, $R^1$, $R^2$, $R^3$, and $R^4$ individually represent a $C_1$–$C_4$ alkyl group,

----- represents a single bond or double bond, and m is 0 or 1.

12. The method according to claim 11, wherein m is 0.
13. The method according to claim 11, wherein m is 1.
14. The method according to claim 11, wherein when m is 0, X and Y individually represent a hydrogen atom, alkyl group, amino group, amide group, carbamoyl group, carboxyl group, keto group, hydroxyl group, sulfonic acid group, phenyl group, acetoxyl group, or acetoamino group, and when m is 1, X and Y individually represent a hydrogen atom, alkyl group, amino group, amide group, carbamoyl group, carboxyl group, keto group, hydroxyl group, sulfonic acid group, phenyl group, or acetoamino group, R is a $C_1$–$C_3$ alkyl group or a phenyl group, $R^1$, $R^2$, $R^3$, and $R^4$ individually represent a $C_1$–$C_4$ alkyl group, and

----- represents a single bond or double bond, provided that when both X and Y are a hydrogen atom, R is neither a phenyl group nor a methyl group, and when X is a hydrogen atom and Y is a hydroxyl group, R is not a methyl group.

15. An N-acyloxylated cycloalkyl compound represented by the following formula (II'):

(II')

wherein m is 0 or 1,
and when m is 0, X' and Y' individually represent a hydrogen atom, alkyl group, amino group, amide group, carbamoyl group, carboxyl group, keto group, hydroxyl group, sulfonic acid group, phenyl group, acetoxyl group, or acetoamino group, and when m is 1, X' and Y' individually represent a hydrogen atom, alkyl group, amino group, amide group, carbamoyl group, carboxyl group, keto group, hydroxyl group, sulfonic acid group, phenyl group, or acetoamino group, R is a $C_1$–$C_3$ alkyl group or a phenyl group, $R^1$, $R^2$, $R^3$, and $R^4$ individually represent a $C_1$–$C_4$ alkyl group, and

----- represents a single bond or double bond, provided that when both X' and Y' are a hydrogen atom, R is neither a phenyl group nor a methyl group, and when X' is a hydrogen atom and Y' is a hydroxyl group, R is not a methyl group.

16. The compound according to claim 15, wherein m is 0.
17. The compound according to claim 15, wherein m is 1.
18. The compound according to claim 15, wherein

----- represents a single bond.

19. The compound according to claim 18, wherein

----- represents a double bond.

20. The compound according to claim 15, wherein X' and Y' are both a hydrogen atom, and R is neither a phenyl group nor a methyl group.
21. The method according to claim 8, wherein said detecting further comprises using contrasting ESR or NMR.
22. A method of scavenging active oxygen or free radicals in a biological tissue or tissues, comprising:

homogenizing a biological tissue or tissue to prepare a homogenized sample; and contacting said homogenized sample with an N-acyloxylated cycloalkyl compound shown by the following formula (I), (I)

wherein A represents a $C_4$ or $C_5$ alkylene group, wherein A may have one ring double bond, and wherein A may be substituted with a substituent selected from the group consisting of an alkyl group, amino group, amide group, carbamoyl group, carboxyl group, keto group, hydroxyl group, sulfonic acid group, phenyl group, acetoxyl group, and acetoamino group, and R is a $C_1$–$C_3$ alkyl group or phenyl group.

23. The method according to claim 8, which comprises treating or diagnosing ischemic diseases, digestive diseases, cancer, cranial nervous diseases accompanied by nerve degeneration, inflammation, or drug-induced organopathy.

* * * * *